(12) United States Patent
Stalcup et al.

(10) Patent No.: US 11,564,799 B2
(45) Date of Patent: Jan. 31, 2023

(54) PATELLOFEMORAL IMPLANT WITH POROUS INGROWTH MATERIAL AND METHOD OF MANUFACTURING SAME

(71) Applicant: SMed-TA/TD, LLC, Columbia City, IN (US)

(72) Inventors: Gregory C. Stalcup, Fort Wayne, IN (US); Steven Dietzel, Warsaw, IN (US)

(73) Assignee: SMed-TA/TD, LLC, Columbia City, IN (US)

( * ) Notice: Subject to any disclaimer, the term of this patent is extended or adjusted under 35 U.S.C. 154(b) by 136 days.

(21) Appl. No.: 16/705,910

(22) Filed: Dec. 6, 2019

(65) Prior Publication Data

US 2020/0179122 A1    Jun. 11, 2020

Related U.S. Application Data (60) Provisional application No. 62/776,692, filed on Dec. 7, 2018.

(51) Int. Cl.
*A61F 2/30*    (2006.01)
*A61F 2/38*    (2006.01)

(52) U.S. Cl.
CPC ........ *A61F 2/30771* (2013.01); *A61F 2/3859* (2013.01); *A61F 2/3877* (2013.01); *A61F 2002/30011* (2013.01); *A61F 2002/3093* (2013.01); *A61F 2002/30892* (2013.01); *A61F 2002/30967* (2013.01);
(Continued)

(58) Field of Classification Search
CPC .. A61F 2/30771; A61F 2/3859; A61F 2/3877; A61F 2002/30011; A61F 2002/30892; A61F 2002/3093; A61F 2002/30967; A61F 2310/00017; A61F 2310/00023; A61F 2310/00029; A61F 2310/00131; A61F 2310/00173; A61F 2310/00179; A61F 2310/00329; A61F 2002/3092; A61F 2002/30971; A61F 2002/30957; A61F 2002/30878; A61F 2/3094; A61F 2/30767

See application file for complete search history.

(56) References Cited

U.S. PATENT DOCUMENTS 9,095,641 B2    8/2015 Albertorio
2004/0049286 A1 *    3/2004 German ............... A61F 2/30734
                                                         623/20.33
(Continued)

FOREIGN PATENT DOCUMENTS

WO    2011/094748 A1    8/2011

OTHER PUBLICATIONS

Extended European Search Report dated Apr. 3, 2020 for European Patent Application No. 19 21 4130 (8 pages).

*Primary Examiner* — Jacqueline Woznicki
(74) *Attorney, Agent, or Firm* — Taylor IP, P.C.

(57) ABSTRACT

An orthopaedic implant includes: a base including a molding material; a first porous ingrowth material region coupled to the base; a second porous ingrowth material region coupled to the base; and at least one barrier insert coupled to the base, the barrier insert including a barrier material that is configured to prevent introduction of the molding material of the base into some pores of the first porous ingrowth material region and some pores of the second porous ingrowth material region during molding of the base.

21 Claims, 11 Drawing Sheets

(52) U.S. Cl.
CPC ............ *A61F 2310/00017* (2013.01); *A61F 2310/00023* (2013.01); *A61F 2310/00029* (2013.01); *A61F 2310/00131* (2013.01); *A61F 2310/00173* (2013.01); *A61F 2310/00179* (2013.01); *A61F 2310/00329* (2013.01)

(56) References Cited

U.S. PATENT DOCUMENTS

| | | | |
|---|---|---|---|
| 2011/0094748 A1* | 8/2011 | Bertele | A61F 2/30734 |
| 2014/0277517 A1* | 9/2014 | Winslow | B29C 43/18 623/19.11 |
| 2018/0055641 A1 | 3/2018 | Jones et al. | |
| 2018/0289493 A1* | 10/2018 | Mansmann | A61F 2/30756 |
| 2019/0184058 A1* | 6/2019 | Aihara | C22C 1/08 |

* cited by examiner

PATELLOFEMORAL IMPLANT WITH POROUS INGROWTH MATERIAL AND METHOD OF MANUFACTURING SAME

CROSS REFERENCE TO RELATED APPLICATIONS

This is a non-provisional application based upon U.S. Provisional Patent Application Ser. No. 62/776,692, entitled "PATELLOFEMORAL IMPLANT WITH POROUS INGROWTH MATERIAL AND METHOD OF MANUFACTURING THE SAME", filed Dec. 7, 2018, which is incorporated herein by reference.

BACKGROUND OF THE INVENTION

1. Field of the Invention

The present disclosure relates to patellofemoral implants and, more particularly, to patellofemoral implants incorporating porous ingrowth material and methods of manufacturing such implants.

2. Description of the Related Art

Orthopaedic implants are known that include one or more porous regions to facilitate and encourage tissue ingrowth to fixate the implant once implanted in a subject. Including such porous regions improves fixation of the implant to reduce the risk of the implant coming loose and failing. While such implants are effective, economically producing the implants with the porous regions is difficult due to the need to preserve the pores while also stably coupling the porous regions to, for example, a base that has a higher material strength and can endure the load exerted on the implant following implantation.

What is needed in the art is an economical way to produce an orthopaedic implant that includes one or more porous material regions.

SUMMARY OF THE INVENTION

Exemplary embodiments disclosed herein provide patellofemoral implants that have porous ingrowth material on one or more surfaces of the implant and methods to manufacture such implants.

In some exemplary embodiments provided according to the present disclosure, an orthopaedic implant includes: a base comprising a molding material; a first porous ingrowth material region coupled to the base; a second porous ingrowth material region coupled to the base; and at least one barrier insert coupled to the base, the barrier insert comprising a barrier material that is configured to prevent introduction of the molding material of the base into some pores of the first porous ingrowth material region and some pores of the second porous ingrowth material region during molding of the base.

One possible advantage that may be realized by exemplary embodiments disclosed herein is that the porous ingrowth material regions can be coupled to a molded base without filling some of the pores of the ingrowth material regions to provide pores for tissue ingrowth.

Another possible advantage that may be realized by exemplary embodiments disclosed herein is that the implants can be produced by, for example, compression molding in an economical fashion.

Yet another possible advantage that may be realized by exemplary embodiments disclosed herein is that the implants can be formed in a variety of shapes for use in different surgical techniques.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
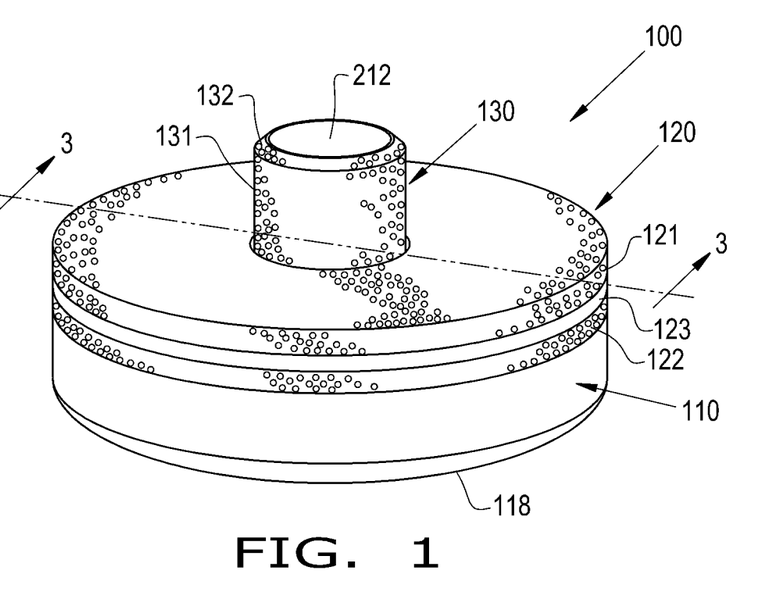
FIG. 1 is a perspective view of an exemplary embodiment of an orthopaedic implant, provided according to the present disclosure.
Figure 2:
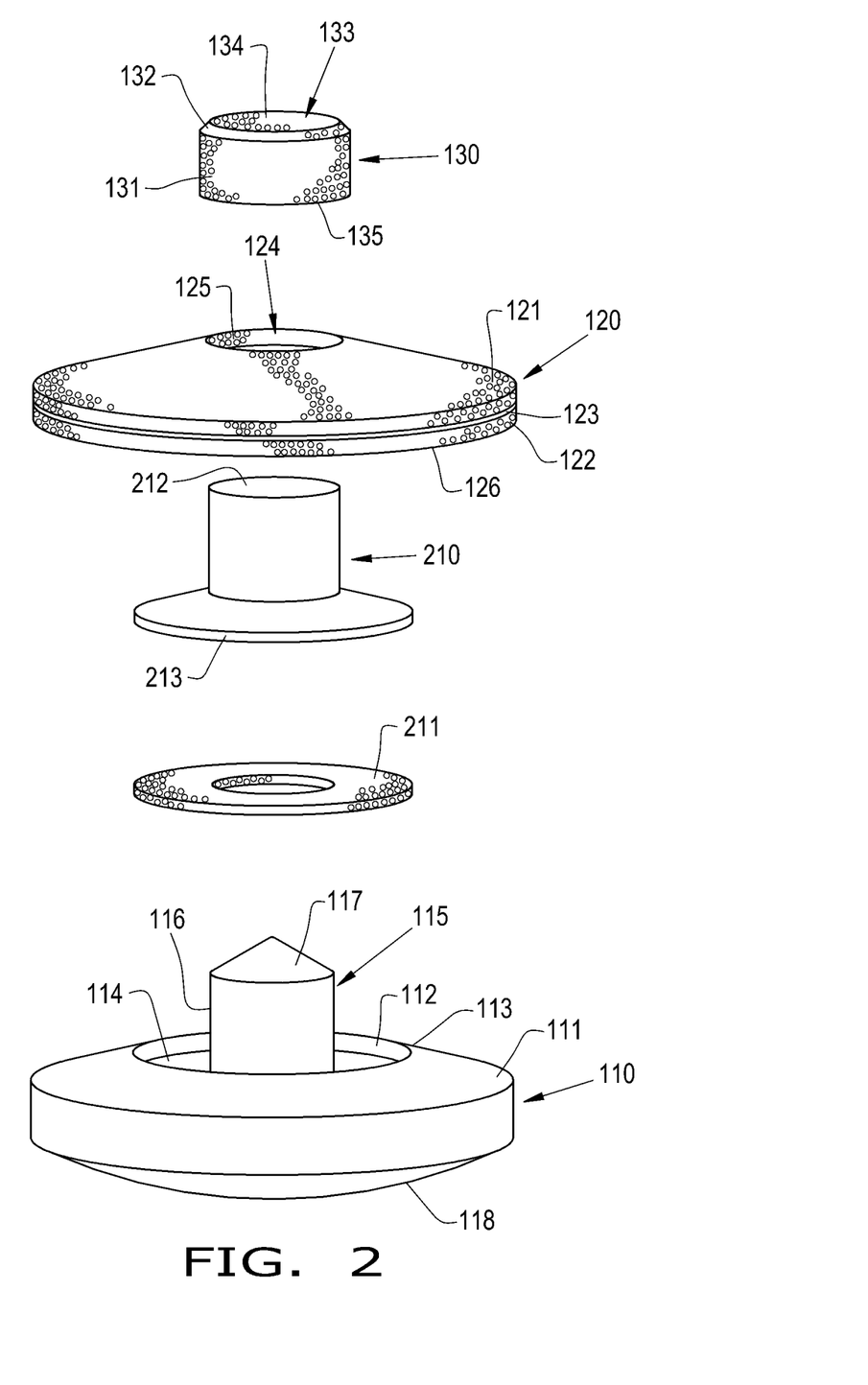
FIG. 2 is an exploded view of the orthopaedic implant of FIG. 1.
Figure 3:
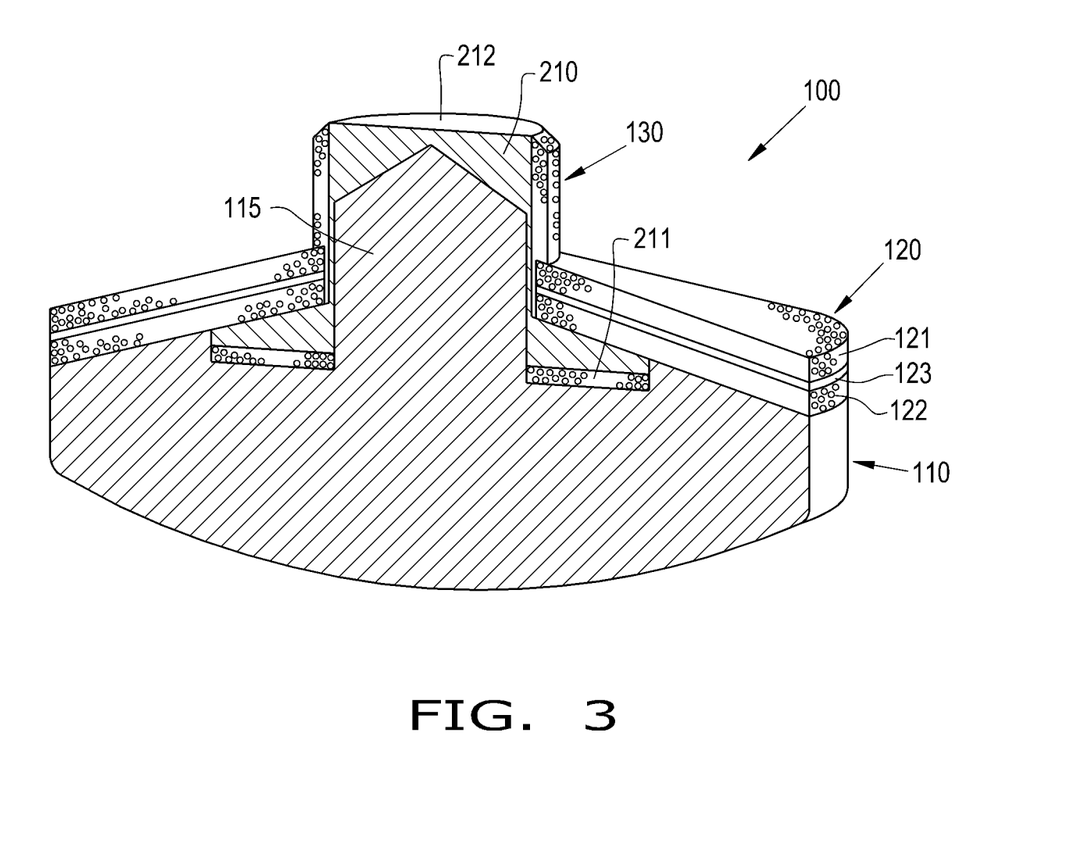
FIG. 3 is a cross-sectional view of the orthopaedic implant of FIG. 3 taken along line 3-3.

Referring now to the drawings, and more particularly to FIGS. 1-3, an exemplary embodiment of a patellofemoral implant 100 is illustrated that generally includes a base 110, a first porous ingrowth material region 120 coupled to the base 110, and a second ingrowth material region 130 coupled to the base 110. As illustrated in, for example, FIG. 2, the base 110 comprises a molding material and may include a domed ring 111 with a recess 112 formed in a top surface 113 of the ring 111. The recess 112 may have a planar bottom 114 with a stem 115 extending therefrom. In some embodiments, the stem 115 includes a cylindrical first portion 116 connected to the bottom 114 of the recess 112 and a conical second portion 117 connected to the first portion 116. In some embodiments, the stem 115 is hollow so the stem 115 can be easily cut through during, for example, a revision surgery. The base 110 may also include a domed bottom 118 that is shaped to act as an articulating surface in, for example, a resected patella. In this sense, the size and shape of the base 110 may be adjusted as needed to fit to different anatomical geometries. In some embodiments, the base 110 comprises a porous biocompatible material that has relatively high strength in order to withstand high loads exerted on the base 110 by surrounding anatomical structures following implantation. Exemplary materials that may be used to form the base 110 include, but are not limited to: metals such as titanium, stainless steel, cobalt chrome, and/or tantalum; polymers such as ultra-high molecular weight polyethylene (UHMWPE), other forms of polyethylene, polyaryl ether ketone (PAEK) such as polyether ether ketone (PEEK), polylactic acid (PLA), and/or polyglycolic acid (PGA); and/or ceramics such as hydroxyapatite (HA), high-density alumina, so-called "Bioglass," and graphite.

The first porous ingrowth material region 120 is coupled to the base 110 to provide a region that encourages cell and tissue ingrowth, and thus fixation of the implant 100 at the implant site. Exemplary materials that may be used to form the material region 120 are similar to materials used to form the base 110 and include, but are not limited to, porous titanium, PEEK, or tantalum. The porosity of the material region 120 may be varied to alter tissue ingrowth characteristics into the material region 120. The porosity of the material region 120 may be, for example, between 30% and 70% to encourage tissue ingrowth into the material region 120. An exemplary material that may be used to form the material region 120 is commercially available under the tradename OSTEOSYNC® from SITES MEDICAL® of Columbia City, Ind. It should be appreciated that a wide variety of porous, biocompatible materials may be used to form the material region 120 to encourage fixation of the implant 100.

In some embodiments, the material region 120 is formed as a composite region with a first ingrowth disc 121 coupled to a second ingrowth disc 122 by a substantially non-porous barrier layer 123 disposed between the discs 121, 122. As used herein, the barrier layer 123 may be "substantially non-porous" if the barrier layer 123 has a porosity of less than 10% and/or a maximum pore size of the pores of the barrier layer 123 is less than 1 mm, such as between 25 µm and 750 µm. In some embodiments, the discs 121, 122 and the barrier layer 123 are coupled to one another using diffusion bonding or another type of suitable bonding. Each of the discs 121, 122 may comprise any of the previously described ingrowth materials and be formed as a domed disc. The second disc 122 may be formed with a shape that is complementary to the top surface 113 of the ring 111 of the base 110 and the first disc 121 may be formed with a shape that is complementary to the second disc 122. The barrier layer 123 may be, for example, a non-porous metal this is diffusion bonded between the discs 121, 122 or a polymer material that is molded between the discs 121, 122 such that the barrier layer 123 prevents pores of the discs 121, 122 from being infiltrated by flowing material. In this sense, the barrier layer 123 protects porous regions of the discs 121, 122 from being filled, maintaining the porosity. In some embodiments, a thickness of the barrier layer 123 is relatively small, such as between about 0.1 mm and about 3.0 mm. The discs 121, 122, on the other hand, may each have a greater thickness than the barrier layer 123, such as between about 0.25 mm and about 6.0 mm.

The discs 121, 122 and barrier layer 123 may each have a respective stem opening formed therein, with the stem openings aligning to form a opening 124 (first illustrated in FIG. 2) extending from a top 125 of the material region 120 to a bottom 126 of the material region 120. The opening 124 may hold the stem 115 of the base 110 therein, as will be described further herein. The opening 124 may define an opening diameter that is greater than a stem diameter of the stem 115.

The second porous ingrowth material region 130 is also coupled to the base 110 to provide a region that encourages cell and tissue ingrowth, and thus fixation of the implant 100 at the implant site. The material region 130 may comprise similar materials to the previously described material region 120. In some embodiments, the material region 130 has a domed shape. In some embodiments, the material region 130 includes a cylindrical portion 131 that is placed adjacent to the material region 120 and a tapered portion 132 that is connected to the cylindrical portion 131. An opening 133 may be formed through the material region 130 that extends from a top 134 of the material region 130 to a bottom 135 of the material region 130. The opening 133 may have an opening diameter that is greater than the stem diameter of the stem 115, similarly to the opening 124. In some embodiments, the opening 133 and the opening 124 have the same diameter.

Referring specifically now to FIGS. 2-3, the implant 100 may further include at least one barrier insert 210 that protects pores of the first porous ingrowth material region 120 and the second porous ingrowth material region 130. The barrier insert 210 may comprise, for example, a barrier material that is a non-porous metal or polymer material or a porous metal or polymer material. In some embodiments, the barrier material is porous and has pores with a maximum pore of no more than 1 mm, such as between 25 µm and 750 µm. In some embodiments, the barrier insert 210 is attached to a porous binding ring 211. The stem 115 of the base 110 may be held in a stem 212, which may also be referred to as a "barrier stem," of the barrier insert 210 and the binding ring 211 may be held in the recess 112 formed in the base 110. In some embodiments, the binding ring 211 comprises a similar porous material to the material regions 120, 130. The binding ring 211 may be, for example, adhered to the base 110 by diffusion bonding or an adhesive or other material to promote binding of the barrier insert 210 to the base 110, as will be described further herein. The stem 212 of the barrier insert 210 may be a hollow cylinder and partially exposed through the opening 133 of the material region 130. In some embodiments, the stem 212 extends from a closed bottom 213 of the barrier insert 210 that is closed to prevent molding material of the base 110 to pass through the bottom 213 during molding.

To form the implant 100, a sheet of material, which may comprise titanium, is prepared. The sheet may be formed as a composite including two or more layers, such as the material of the discs 121, 122 with material of the barrier layer 123 diffusion bonded or otherwise disposed therebetween. A disc approximating the shape of the material region 120 is removed, such as laser cut, from the formed sheet and formed into the domed shape by, for example, pressing the cut shape against a domed block to form the material region 120 with a domed shape. The opening 124 may also be formed in the material of the formed sheet before, during, or after removal. The barrier insert 210 may be machined from, for example, a non-porous material, such as titanium, separately from the material region 120. The material region 130 may also be formed by machining a porous material into the desired shape. The binding ring 211 may be formed by, for example, cutting the shape of the binding ring 211 from a porous material, such as porous titanium.

The barrier insert 210 and the binding ring 211 are attached to one another. The binding ring 211 may, for example, be diffusion bonded to the bottom of the barrier insert 210 to form an intermediate assembly. The ingrowth material regions 120, 130 are positioned such that they fit over the stem 212 of the barrier insert 210 of the intermediate assembly. The ingrowth material regions 120 and 130 may then be diffusion bonded with the intermediate assembly. Before or after diffusion bonding of the ingrowth material regions 120, 130 with the intermediate assembly, an opening may be drilled or otherwise formed into the stem 212 of the barrier insert 210 so the stem 212 is a hollow stem.

The diffusion bonded ingrowth material regions 120, 130 and intermediate assembly may then be placed in a mold. Melted molding material, which may be a polymer such as UHMWPE, is introduced into the mold and flows through the opening formed in the stem 212 to form the base 110 and bond the components of the implant 100 together. The melted molding material may be introduced by, for example, compression molding. The barrier insert 210, owing to the nature of the barrier material forming the barrier insert 210, protects some of the pores of the material regions 120, 130 from filling with molding material as the melted material is introduced, leaving some porous regions of the material regions 120, 130 open to tissue ingrowth. In other words, the barrier material is configured to prevent introduction of the molding material of the base 110 into some pores of the first porous ingrowth material region 120 and some pores of the second porous ingrowth material region 130 during molding of the base 110. Other portions of the implant 100, such as the disc 122, the binding ring 211, and the hollow stem 212, fill with the introduced molding material, which cools to bond the components of the implant 100 together and form the final implant 100.

From the foregoing, it should be appreciated that the implant 100 may be formed in a rapid fashion that securely binds the porous ingrowth material regions 120, 130 together with the molded base 110. By protecting pores of various elements of the implant 100 with the barrier insert 210, secure bonding can be achieved while also maintaining high porosity for tissue ingrowth. Further, the shapes of the barrier insert 210 and the material regions 120, 130, as well as the base 110 formed during molding, allow the components to be properly oriented relative to one another in a relatively simple and quick manner. It should thus be appreciated that the present disclosure provides an implant 100 that may be rapidly and easily manufactured, which may reduce cost.

In some embodiments, the base 110 is pre-formed and is not formed by molding while introducing melted material into the stem 212. In such embodiments, the base 110 may be attached to the other components of the implant 100 by, for example, diffusion bonding or mechanical attachment.

Figure 4:
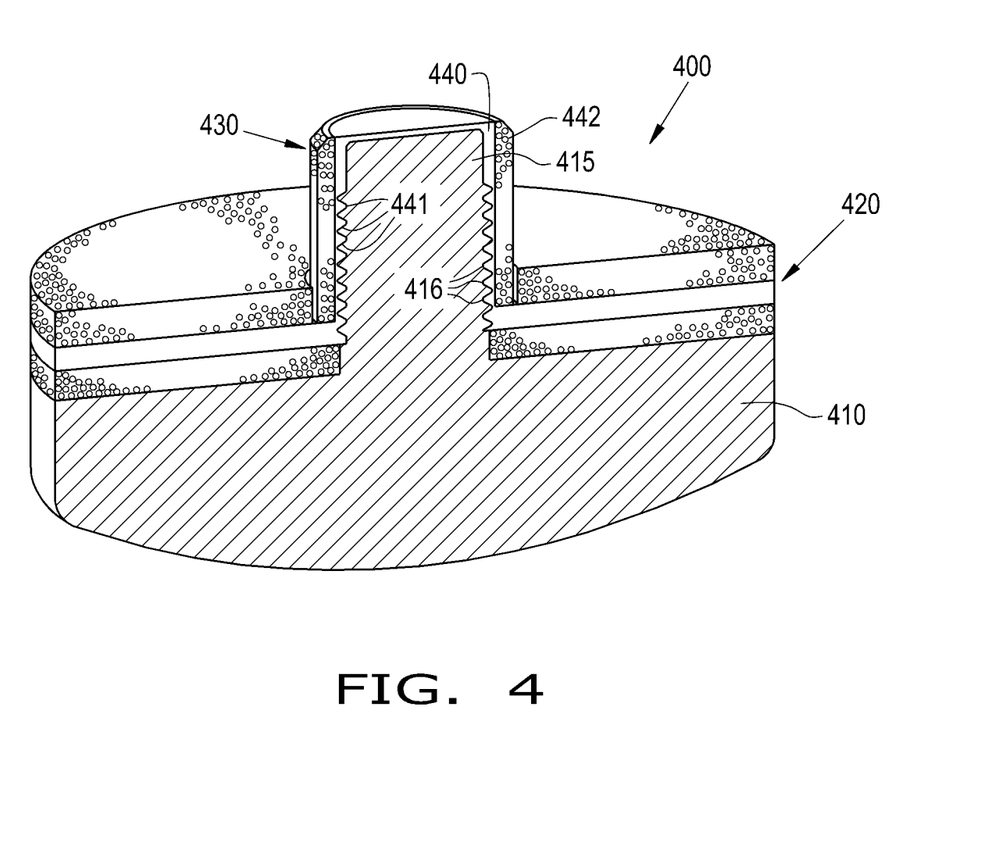
FIG. 4 is a cross-sectional view of an exemplary embodiment of an orthopaedic implant including a barrier insert with molding grooves, provided according to the present disclosure.

Referring now to FIG. 4, another exemplary embodiment of an implant 400 is illustrated that includes a barrier insert 440 with molding grooves 441 formed therein. The molding grooves 441 may be formed, for example, in a barrier stem 442 of the barrier insert 440. The molding grooves 441 allow material infiltration of molding material of a base 410 formed during molding to produce a base stem 415 with locking protrusions 416, which securely couple the barrier insert 440 to the base 410. In other respects, the implant 400 may be structured and formed similarly to the implant 100 illustrated in FIGS. 1-3, such as including porous ingrowth material regions 420 and 430, so further description is omitted for the sake of brevity.

Figure 5:
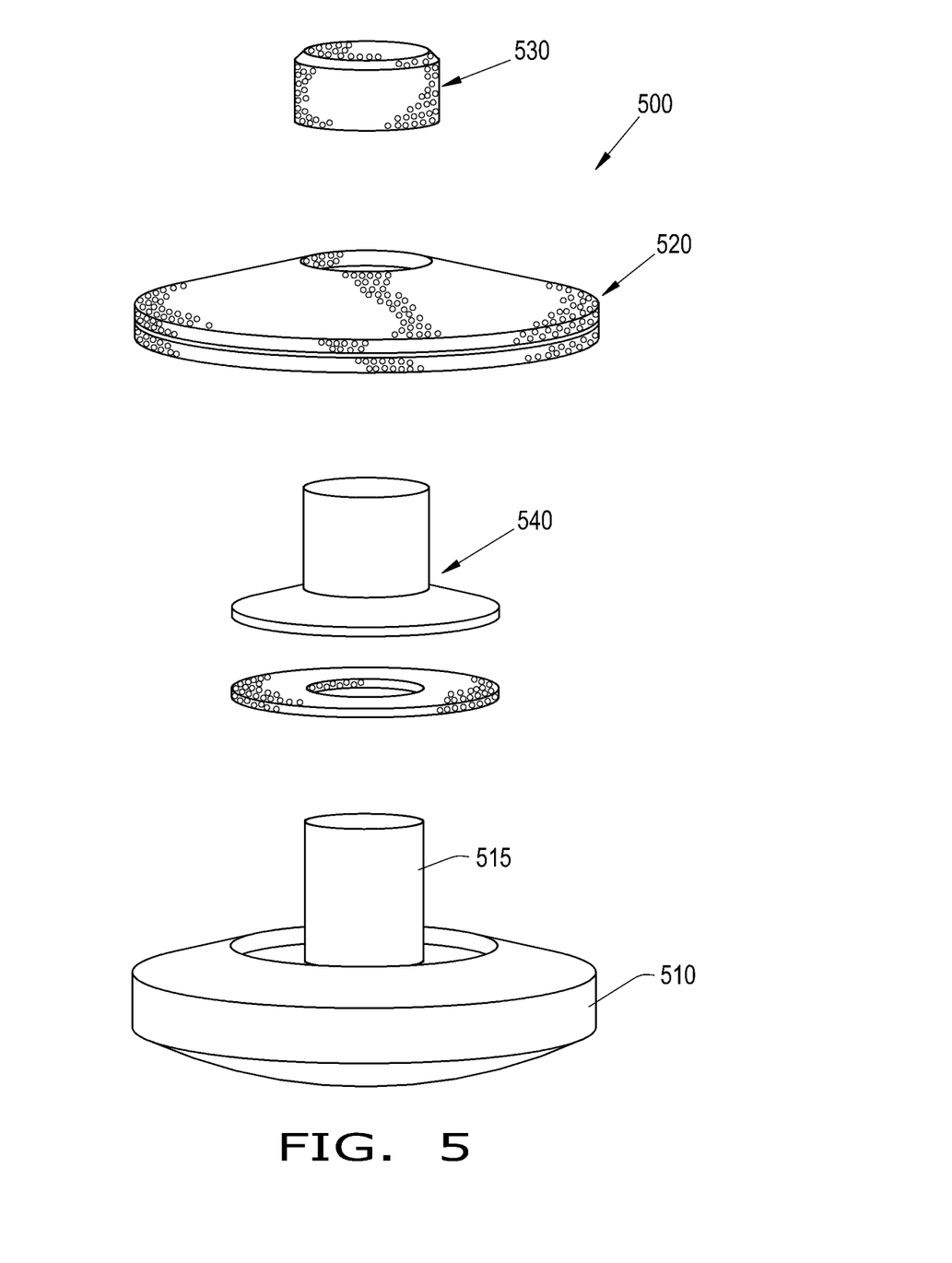
FIG. 5 is an exploded view of an exemplary embodiment of an orthopaedic implant, provided according to the present disclosure.

Referring now to FIG. 5, another exemplary embodiment of an implant 500 is illustrated that includes a base 510 with a substantially cylindrical stem 515. The implant 500 includes a first porous ingrowth material region 520 and a second porous ingrowth material region 530 bonded to the base 510 with pores protected by a barrier insert 540. It should thus be appreciated that, other than having a base 510 with a cylindrical stem 515, the implant 500 may be structured and formed similarly to the previously described implants 100, 400, so further description is omitted for the sake of brevity.

Figure 6:
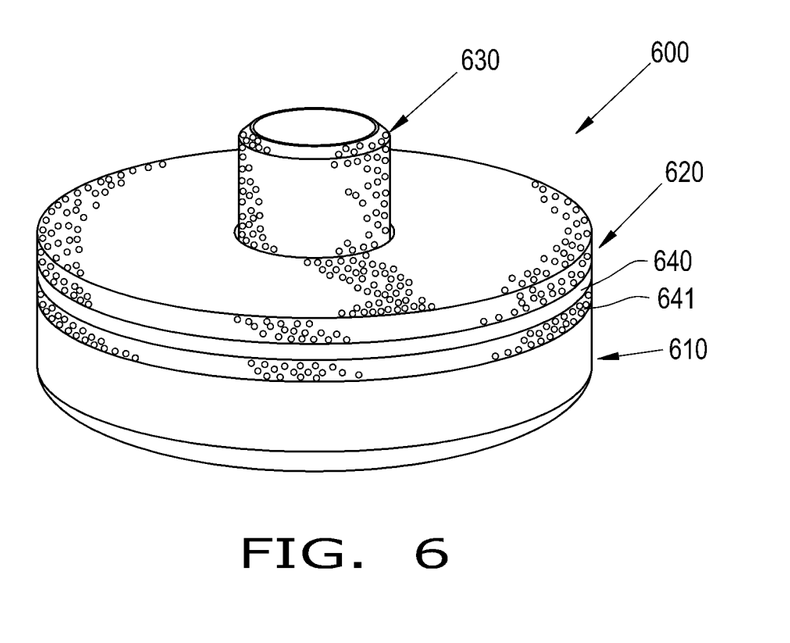
FIG. 6 is a perspective view of an exemplary embodiment of an orthopaedic implant, provided according to the present disclosure.
Figure 7:
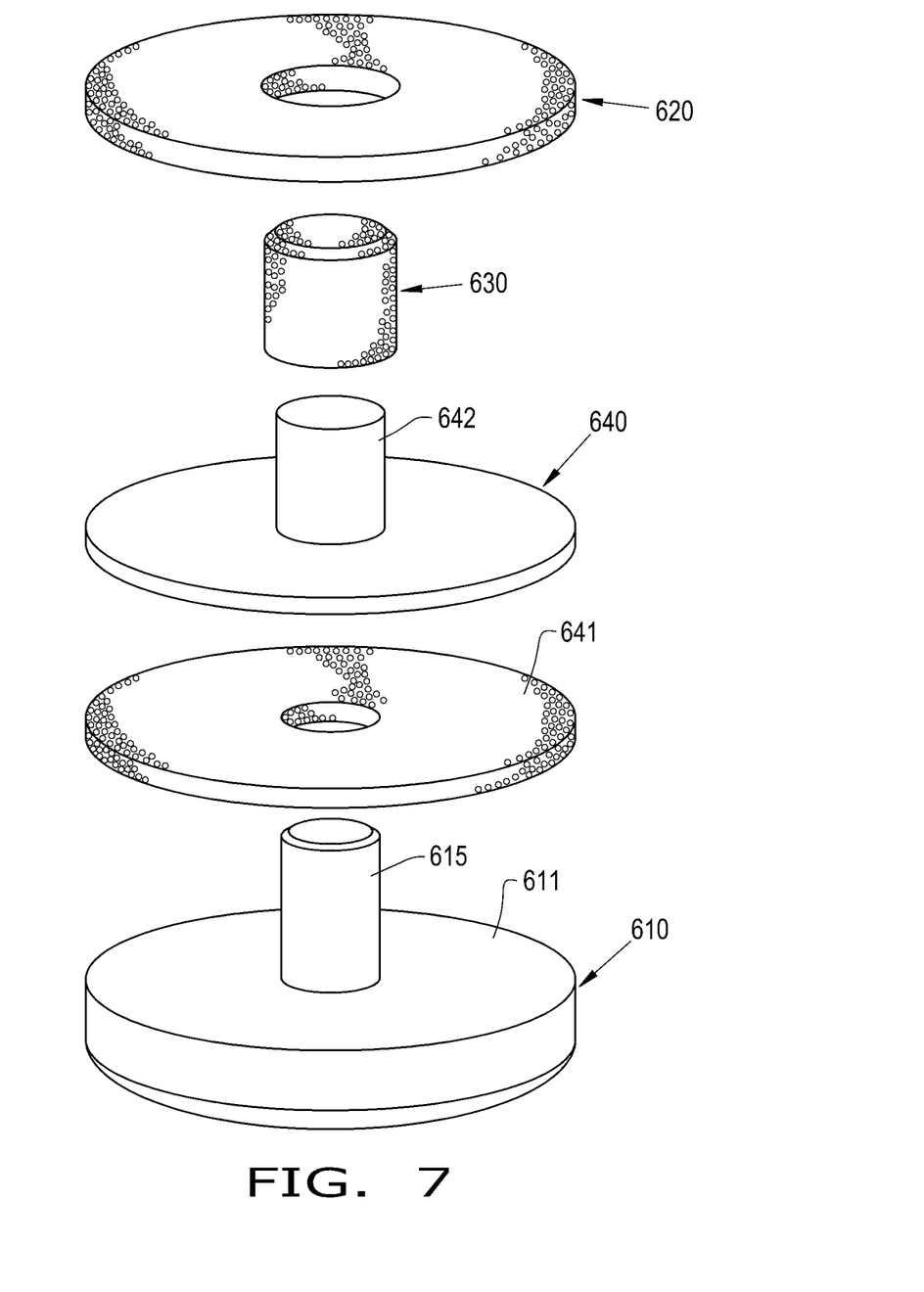
FIG. 7 is an exploded view of the orthopaedic implant of FIG. 6.

Referring now to FIGS. 6-7, another exemplary embodiment of an implant 600 is illustrated that includes a base 610 formed without a recess. The implant 600 further includes a first porous ingrowth material region 620 and a second porous ingrowth material region 630 coupled to the base 610 with pores protected by a barrier insert 640, which may bind to a binding ring 641. The material region 620 may be formed as a flat ring, i.e., non-domed, and resemble the shape of a washer. The binding ring 641 may be formed similarly to the material region 620 and bonded to a flat top surface 611 of the base 610 during molding. The material regions 620, 630 are fit over a molding stem 642 of the barrier insert 640 and melted material introduced to bond the material regions 620, 630 together and form the base 610. The barrier insert 640 protects some pores of the material regions 620, 630. Thus, the material regions 620, 630 securely bond to each other (and the formed base 610) and form the implant 600 without a significant filling of some or all of the pores of the material regions 620, 630, similarly to the previously described implants 100, 400, 500. In other respects, the implant 600 may be structured and formed similarly to the previously described implants 100, 400, 500, so further description is omitted for the sake of brevity.

Figure 8:
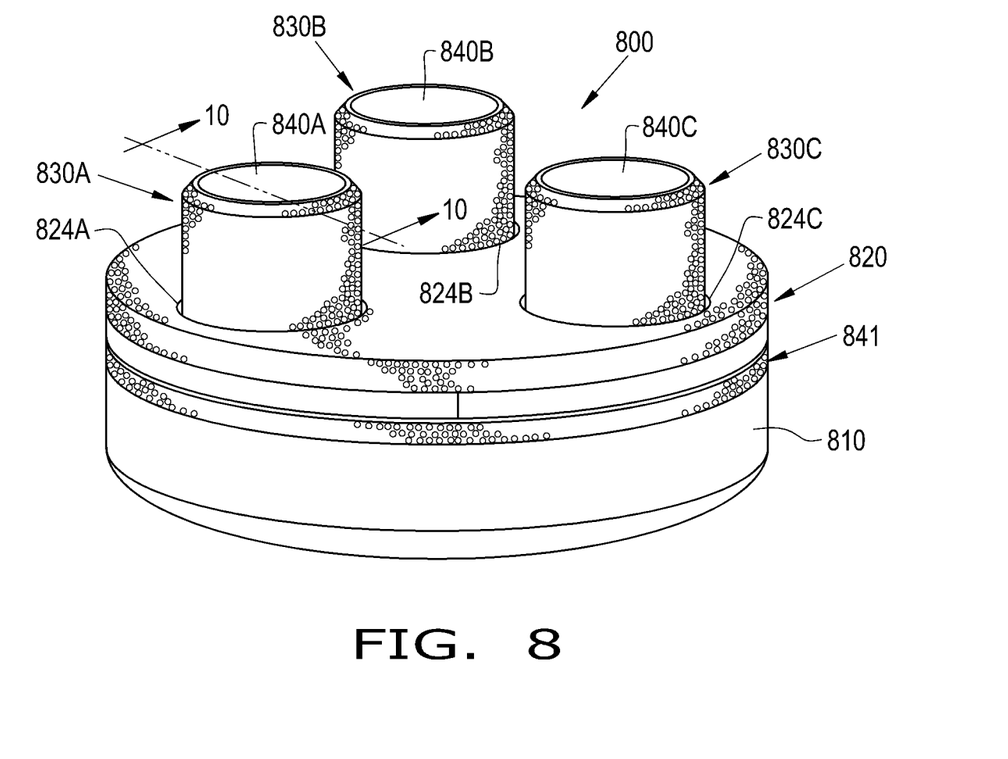
FIG. 8 is a perspective view of an exemplary embodiment of an orthopaedic implant including multiple barrier inserts, provided according to the present disclosure.
Figure 9:
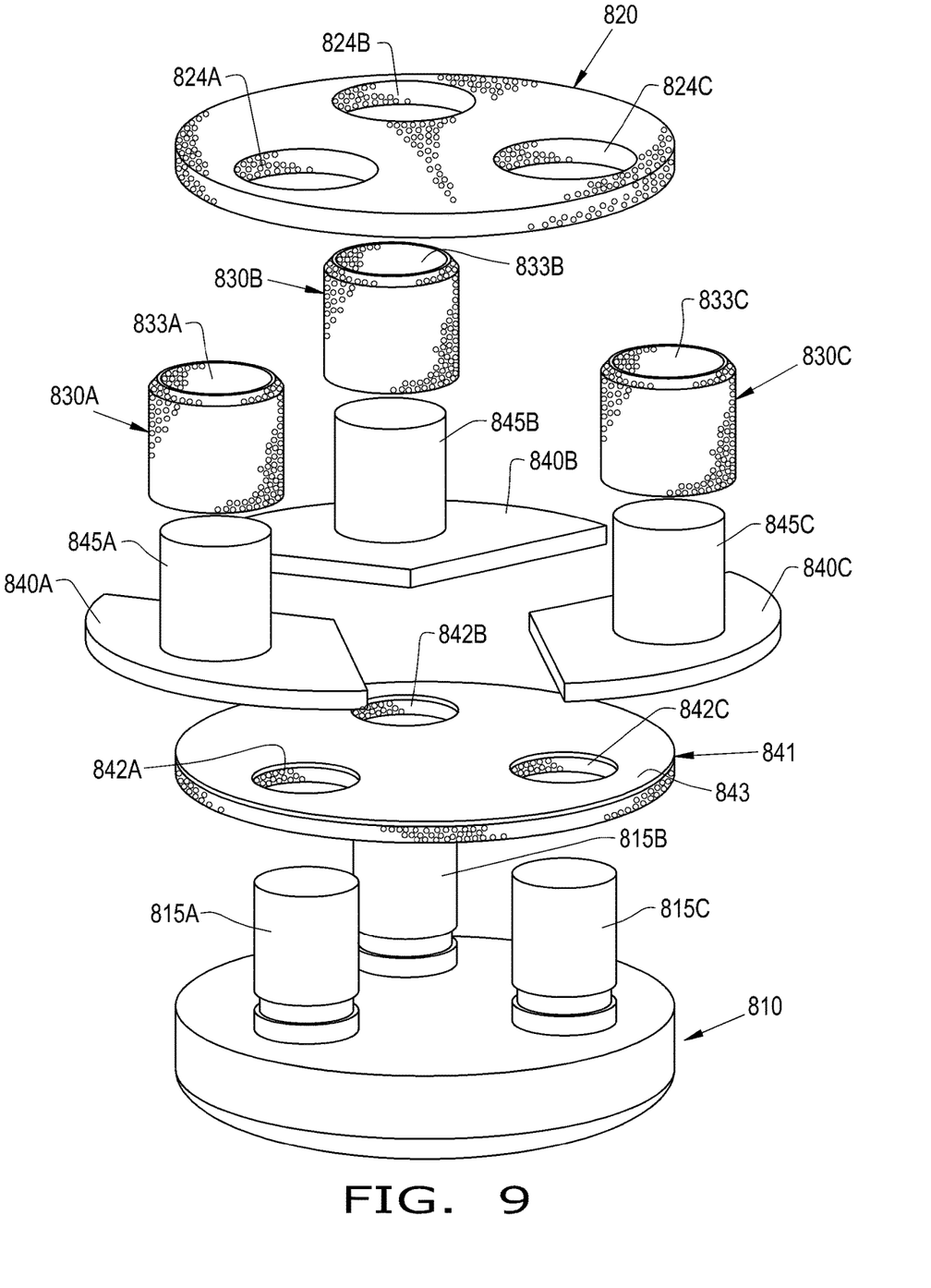
FIG. 9 is an exploded view of the orthopaedic implant of FIG. 8.
Figure 10:
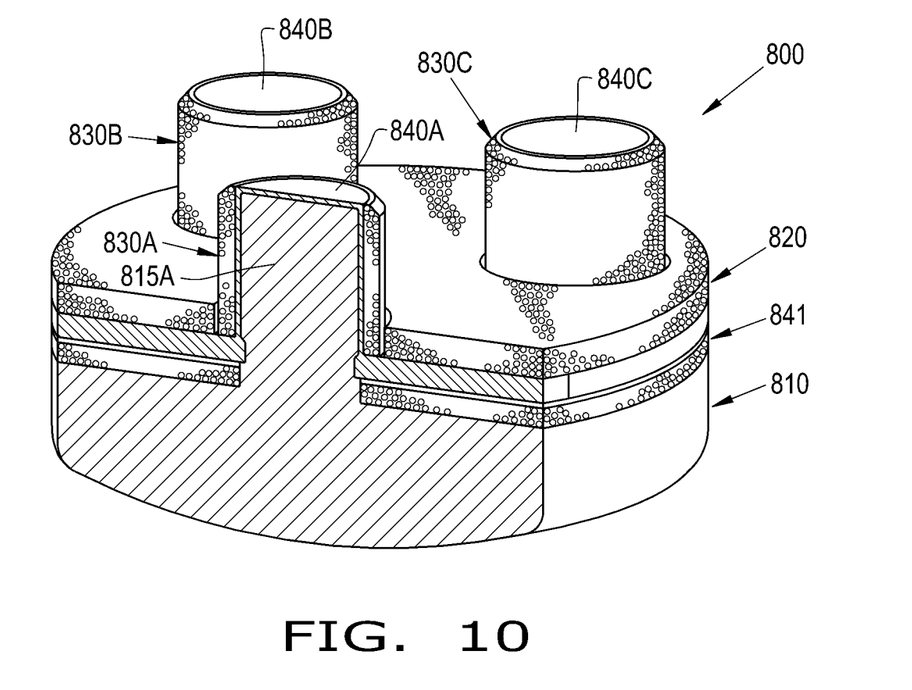
FIG. 10 is a cross-sectional view of the orthopaedic implant of FIG. 8 taken along line 10-10.

Referring now to FIGS. 8-10, another exemplary embodiment of an implant 800 is illustrated that includes a base 810 including three spaced-apart stems 815A, 815B, 815C. The implant 800 also includes a first porous ingrowth material region 820 and a plurality of second porous ingrowth material regions, illustrated as three material regions 830A, 830B, 830C, coupled to the base 810. The material region 820 may be formed as a substantially flat ring with a plurality of openings 824A, 824B, 824C formed therein. The material regions 830A, 830B, 830C may each be formed as a cylinder with a respective opening 833A, 833B, 833C. In some embodiments, the openings 824A, 824B, 824C of the material region 820 each define a respective opening diameter that is larger than a region diameter of a corresponding material region 830A, 830B, 830C so each of the material regions 830A, 830B, 830C fits within a respective opening 824A, 824B, 824C. A plurality of barrier inserts 840A, 840B, 840C may protect pores of the material regions 820, 830A, 830B, 830C during molding of the base 810. A binding ring 841 may bind to a top surface 811 of the base 810. The binding ring 841 may be formed of a similar material as the material regions 820, 830A, 830B, 830C and have a plurality of openings 842A, 842B, 842C and, in some embodiments, a non-porous top surface 843.

To form the implant 800, a sheet of material, which may comprise titanium, is prepared. The material region 820 may be separated from the sheet and the openings 824A, 824B, 824C formed in the material region 820 by, for example, laser cutting. The material regions 830A, 830B, 830C may be formed by, for example, machining. The barrier inserts 840A, 840B, 840C may also be formed by machining. Each of the barrier inserts 840A, 840B, 840C may be formed with a respective stem 845A, 845B, 845C and abut against at least one adjacent barrier insert 840A, 840B, 840C.

The barrier inserts 840A, 840B, 840C are attached to the binding ring 841 by, for example, diffusion bonding to form an intermediate assembly. The material region 820 is positioned so each stem 845A, 845B, 845C of the barrier inserts 840A, 840B, 840C extends through a respective opening 824A, 824B, 824C and the material regions 830A, 830B, 830C are placed over a respective one of the stems 845A, 845B, 845C. The material regions 820, 830A, 830B, 830C and intermediate assembly may then be attached together, such as by diffusion bonding, and openings may be formed in each of the stems 845A, 845B, 845C so the stems 845A, 845B, 845C are each hollow.

The diffusion bonded material regions 820, 830A, 830B, 830C and intermediate assembly may then be placed in a mold. Melted material, which may be a polymer such as UHMWPE, is introduced into the mold and flows through the openings formed in the stems 845A, 845B, 845C to form the base 810 and bond the components of the implant 800 together. The melted material may be introduced by, for example, compression molding. The barrier inserts 840A, 840B, 840C, owing to their non-porous nature, protect some of the pores of the material regions 820, 830A, 830B, 830C from filling with material as the melted material is introduced, leaving some porous regions of the material regions 820, 830A, 830B, 830C open to tissue ingrowth. Other portions of the implant 800, such as a bottom of the binding ring 841, and the hollow stems 845A, 845B, 845C of the barrier inserts 840A, 840B, 840C, fill with the introduced material, which cools to bond the components of the implant 800 together and form the final implant 800.

From the foregoing, it should be appreciated that the implant 800 may be formed similarly to the previously described implants 100, 400, 500, 600, but include more than one stem. Additional stems may be useful when, for example, a larger implant size is needed to repair a defect in a bone. Thus, it should be further appreciated that implants may be formed in accordance with the present disclosure that include multiple stems and have different sizes to meet different surgical requirements.

Figure 11:
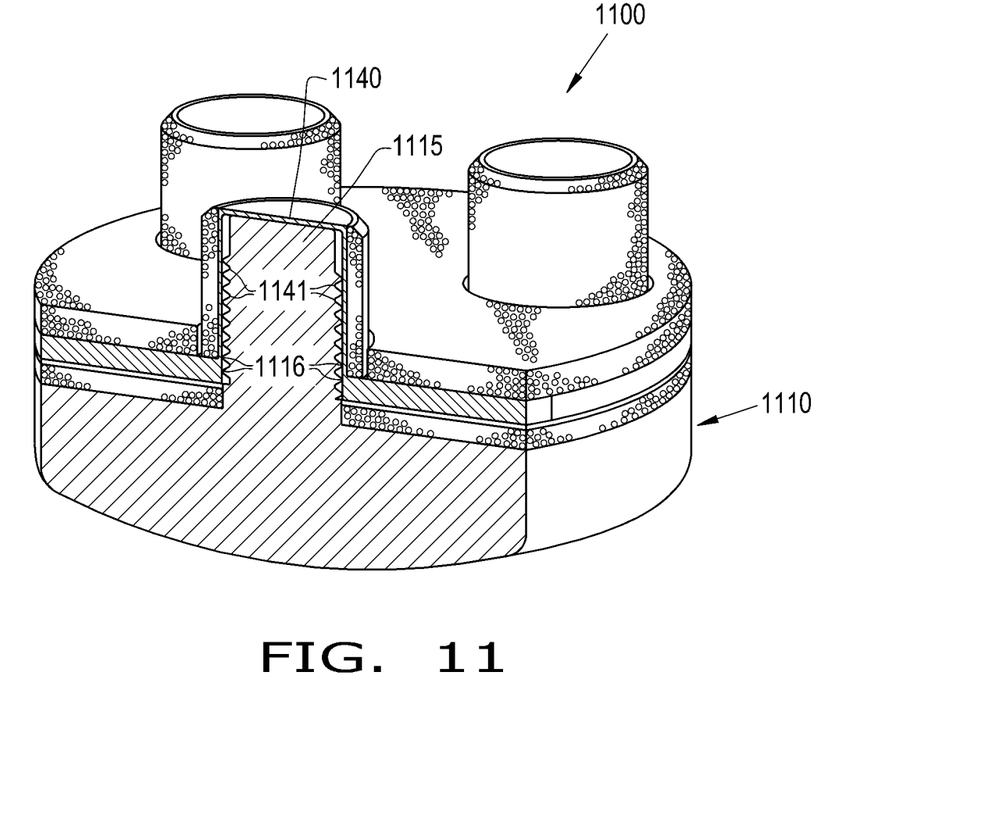
FIG. 11 is a cross-sectional view of an exemplary embodiment of an orthopaedic implant including multiple barrier inserts and molding grooves in at least one of the barrier inserts, provided according to the present disclosure.

Referring now to FIG. 11, another exemplary embodiment of an implant 1100 is illustrated that includes three barrier inserts 1140 with hollow stems, similarly to the implant 800, that each have molding grooves 1141. The molding grooves 1141 fill with material during molding to form corresponding molded stems 1115 of a base 1110. The stems 1115 of the base 1110 have molding protrusions 1116 that fill the molding grooves 1141 to securely lock the barrier inserts 1140 and the base 1110 together. In other respects, the implant 1100 may be structured and formed similarly to the implant 800 illustrated in FIGS. 8-10, so further description is omitted for the sake of brevity.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic implant, comprising:
   a base comprising a molding material;
   a first porous ingrowth material region coupled to the base;
   a second porous ingrowth material region coupled to the base; and
   at least one barrier insert coupled to the base, the at least one barrier insert comprising a barrier material that is configured to prevent introduction of the molding material of the base into some pores of the first porous ingrowth material region and some pores of the second porous ingrowth material region during molding of the base, the at least one barrier insert further comprising a barrier stem that is hollow.

2. The orthopaedic implant of claim 1, wherein the base further comprises a hollow stem.

3. The orthopaedic implant of claim 1, wherein the first porous ingrowth material region and the second porous ingrowth material region both fit over the barrier stem.

4. The orthopaedic implant of claim 3, wherein the first porous ingrowth material region and the second porous ingrowth material region are diffusion bonded to the barrier stem.

5. The orthopaedic implant of claim 1, wherein the at least one barrier insert comprises a plurality of molding grooves formed therein.

6. The orthopaedic implant of claim 5, wherein the molding grooves are formed in the barrier stem.

7. The orthopaedic implant of claim 6, wherein the molding material of the base fills at least some of the molding grooves.

8. The orthopaedic implant of claim 1, wherein the barrier stem is exposed through an opening of the second porous ingrowth material region.

9. The orthopaedic implant of claim 1, further comprising a porous binding ring disposed between the at least one barrier insert and the base, the binding ring being at least partially filled with the molding material of the base to bind the at least one barrier insert to the base.

10. The orthopaedic implant of claim 9, wherein the base comprises a recess and the porous binding ring is disposed in the recess.

11. The orthopaedic implant of claim 1, wherein the first porous ingrowth material region comprises a first ingrowth disc, a second ingrowth disc, and a barrier layer coupled to the first ingrowth disc and the second ingrowth disc.

12. The orthopaedic implant of claim 11, wherein the barrier layer comprises a substantially non-porous material.

13. The orthopaedic implant of claim 11, wherein the barrier material comprises a porous material having pores with a maximum pore size of no more than 1 mm.

14. The orthopaedic implant of claim 1, wherein the at least one barrier insert comprises a plurality of barrier inserts.

15. The orthopaedic implant of claim 14, wherein each of the barrier inserts abuts against at least one adjacent barrier insert.

16. The orthopaedic implant of claim 14, wherein each of the barrier inserts comprises a respective barrier stem.

17. The orthopaedic implant of claim 1, wherein the at least one barrier insert comprises a closed bottom.

18. An orthopaedic implant, comprising:
    a base comprising a molding material;
    a first porous ingrowth material region coupled to the base;
    a second porous ingrowth material region coupled to the base; and
    at least one barrier insert coupled to the base, the at least one barrier insert comprising a barrier material that is configured to prevent introduction of the molding material of the base into some pores of the first porous ingrowth material region and some pores of the second porous ingrowth material region during molding of the base, the at least one barrier insert further comprising a barrier stem and a plurality of molding grooves formed in the barrier stem.

19. An orthopaedic implant, comprising:

a base comprising a molding material;

a first porous ingrowth material region coupled to the base;

a second porous ingrowth material region coupled to the base; and at least one barrier insert coupled to the base, the at least one barrier insert comprising a barrier material that is configured to prevent introduction of the molding material of the base into some pores of the first porous ingrowth material region and some pores of the second porous ingrowth material region during molding of the base, the at least one barrier insert further comprising a barrier stem that is exposed through an opening of the second porous ingrowth material region.

20. An orthopaedic implant, comprising:

a base comprising a molding material;

a first porous ingrowth material region coupled to the base;

a second porous ingrowth material region coupled to the base; and at least one barrier insert coupled to the base, the at least one barrier insert comprising a barrier material that is configured to prevent introduction of the molding material of the base into some pores of the first porous ingrowth material region and some pores of the second porous ingrowth material region during molding of the base, the at least one barrier insert further comprising a barrier stem that is exposed through an opening of the second porous ingrowth material region, the barrier material comprising a porous material having pores with a maximum pore size of no more than 1 mm.

21. An orthopaedic implant, comprising:

a base comprising a molding material;

a first porous ingrowth material region coupled to the base;

a second porous ingrowth material region coupled to the base; and a plurality of barrier inserts coupled to the base, the barrier inserts each comprising a barrier material that is configured to prevent introduction of the molding material of the base into some pores of the first porous ingrowth material region and some pores of the second porous ingrowth material region during molding of the base, wherein each of the barrier inserts abuts against at least one adjacent barrier insert.

* * * * *